(12) United States Patent
Eddy (10) Patent No.: US 11,305,033 B2
(45) Date of Patent: Apr. 19, 2022

(54) SPLINTING SYSTEM INCLUDING AN ANTIMICROBIAL COATING AND A METHOD OF MANUFACTURING THE SAME

(71) Applicant: Parasol Medical, LLC, Buffalo Grove, IL (US)

(72) Inventor: Patrick E. Eddy, Allendale, MI (US)

(73) Assignee: Parasol Medical, LLC, Buffalo Grove, IL (US)

( * ) Notice: Subject to any disclaimer, the term of this patent is extended or adjusted under 35 U.S.C. 154(b) by 388 days.

(21) Appl. No.: 16/293,240

(22) Filed: Mar. 5, 2019

(65) Prior Publication Data
US 2020/0282099 A1  Sep. 10, 2020

(51) Int. Cl.
*A61F 5/00* (2006.01)
*A61L 15/14* (2006.01)
(Continued)

(52) U.S. Cl.
CPC ............... *A61L 15/14* (2013.01); *A61L 15/08* (2013.01); *A61L 15/12* (2013.01);
(Continued)

(58) Field of Classification Search
CPC .. A61F 5/058; A61F 5/05866; A61F 5/05825; A61F 5/01; A61F 5/0118;
(Continued)

(56) References Cited

U.S. PATENT DOCUMENTS

| | | | |
|---|---|---|---|
| 4,372,303 A | 2/1983 | Grossmann et al. | |
| 4,394,378 A * | 7/1983 | Klein | C07F 7/1804 514/63 |

(Continued)

FOREIGN PATENT DOCUMENTS

| | | |
|---|---|---|
| WO | 0054587 A1 | 9/2000 |
| WO | 0072850 A1 | 12/2000 |

(Continued)

OTHER PUBLICATIONS

Anonymous, 2009, SiSiB PC9911 Antimicrobial, Power Chemical Corp, [online]; downloaded from URL<http://www.powerchemcorp.com/library/public/SiSiB_PC9911.pdf> on Oct. 8, 2013; 2 pages.

(Continued)

*Primary Examiner* — Kim M Lewis
(74) *Attorney, Agent, or Firm* — Price Heneveld LLP (57) ABSTRACT

A splinting system that includes a curable splint member including layers of fiberglass cloth coated with a water curable resin, and a pad at least partially enveloping the layers of fiberglass cloth, the pad having an exterior surface and an antimicrobial coating applied to the exterior surface; and a metal foil pouch containing the curable splint member, the metal foil pouch including an exterior surface. The antimicrobial coating includes a silane quaternary ammonium ion or salt thereof. The silane quaternary ammonium ion or salt thereof is one or more of: 3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride. The antimicrobial coating can be applied to the curable splint member by applying a solution, which includes 0.1 percent and 10 percent by weight the silane quaternary ammonium ion or salt thereof and an isopropyl alcohol solvent, to the exterior surface of the pad.

6 Claims, 6 Drawing Sheets (51) Int. Cl.
*A61L 15/08* (2006.01)
*A61L 15/12* (2006.01)

(52) U.S. Cl.
CPC ... *A61L 2300/208* (2013.01); *A61L 2300/216* (2013.01); *A61L 2300/404* (2013.01)

(58) Field of Classification Search
CPC ...... A61F 5/0109; A61F 13/04; A61F 13/016; A61F 13/07; A61F 13/12; A61F 13/14; A61F 13/046; A61F 13/00991; A61L 15/08; A61L 15/12; A61L 15/14; A61L 15/07
See application file for complete search history.

(56) References Cited

U.S. PATENT DOCUMENTS

| | | | |
|---|---|---|---|
| 4,865,844 A | 9/1989 | Blank et al. | |
| 4,921,691 A * | 5/1990 | Stockel | A61L 26/0014 424/45 |
| 5,003,970 A * | 4/1991 | Parker | A61F 13/04 206/389 |
| 5,079,004 A | 1/1992 | Blank et al. | |
| 5,183,664 A | 2/1993 | Ansell | |
| 5,270,358 A | 12/1993 | Asmus | |
| 5,428,078 A | 6/1995 | Cohen et al. | |
| 5,520,664 A * | 5/1996 | Bricault, Jr. | A61F 2/30767 604/174 |
| 5,762,623 A | 6/1998 | Murphy et al. | |
| 5,954,869 A | 9/1999 | Elfersy et al. | |
| 5,959,014 A | 9/1999 | Liebeskind et al. | |
| 6,224,579 B1 | 5/2001 | Modak et al. | |
| 6,495,229 B1 | 12/2002 | Carte et al. | |
| 6,821,943 B2 | 11/2004 | Avery et al. | |
| 6,994,890 B2 | 2/2006 | Ohlhausen et al. | |
| 7,045,673 B1 | 5/2006 | Batich et al. | |
| 7,704,313 B2 | 4/2010 | Ohlhausen et al. | |
| 7,709,694 B2 | 5/2010 | Batich et al. | |
| 7,754,004 B2 | 7/2010 | Ohlhausen et al. | |
| 7,790,217 B2 | 9/2010 | Toreki et al. | |
| 8,025,120 B2 | 9/2011 | Eddy | |
| 8,257,780 B2 | 9/2012 | Ohlhausen et al. | |
| 8,440,217 B1 | 5/2013 | El-Naggar et al. | |
| 8,491,922 B2 | 7/2013 | Eddy | |
| 8,639,527 B2 | 1/2014 | Rensvold et al. | |
| 8,679,526 B2 | 3/2014 | Van Den Plas et al. | |
| 9,028,846 B2 | 5/2015 | Eddy | |
| 9,433,708 B2 | 9/2016 | Eddy | |
| 9,675,735 B2 | 6/2017 | Eddy | |
| 9,717,249 B2 | 8/2017 | Eddy | |
| 2002/0111282 A1 | 8/2002 | Charaf et al. | |
| 2007/0021383 A1 | 1/2007 | Loder | |
| 2007/0042198 A1 | 2/2007 | Schonemyr et al. | |
| 2007/0218096 A1 | 9/2007 | Wooley | |
| 2008/0033329 A1 * | 2/2008 | Downs | A61L 15/46 602/41 |
| 2008/0260804 A1 | 10/2008 | Morris et al. | |
| 2009/0215917 A1 | 8/2009 | Trotter et al. | |
| 2009/0223411 A1 | 9/2009 | Higgins et al. | |
| 2009/0252647 A1 | 10/2009 | Orofino | |
| 2009/0312684 A1 | 12/2009 | Leonard et al. | |
| 2010/0028462 A1 | 2/2010 | Bolkan et al. | |
| 2010/0063431 A1 * | 3/2010 | Bae | A61F 13/04 602/5 |
| 2010/0167978 A1 | 7/2010 | Iyer et al. | |
| 2010/0331710 A1 | 12/2010 | Eddy | |
| 2011/0200655 A1 | 8/2011 | Black et al. | |
| 2011/0233810 A1 | 9/2011 | Neigel et al. | |
| 2012/0173274 A1 | 7/2012 | Rensvold et al. | |
| 2013/0101677 A1 | 4/2013 | Callahan et al. | |
| 2013/0231599 A1 * | 9/2013 | Eddy | A61F 13/0253 602/48 |
| 2013/0345170 A1 | 12/2013 | Eddy | |
| 2014/0100504 A1 | 4/2014 | Eddy | |
| 2014/0271794 A1 * | 9/2014 | Eddy | A61L 15/425 424/443 |
| 2015/0005684 A1 * | 1/2015 | Evans | C08L 75/04 602/8 |
| 2016/0143275 A1 | 5/2016 | Lan et al. | |
| 2016/0143276 A1 | 5/2016 | Lan et al. | |
| 2016/0262382 A1 | 9/2016 | Lan et al. | |
| 2016/0262383 A1 | 9/2016 | Lan et al. | |
| 2016/0295858 A1 * | 10/2016 | Mason | A01N 65/28 |
| 2017/0280716 A1 | 10/2017 | Lan et al. | |
| 2018/0055695 A1 * | 3/2018 | Park | A61L 15/14 |
| 2018/0080605 A1 * | 3/2018 | Janway | F16M 13/022 |

FOREIGN PATENT DOCUMENTS

| | | |
|---|---|---|
| WO | 2005042657 A2 | 5/2005 |
| WO | 2007061625 A2 | 5/2007 |
| WO | 2007076413 A2 | 7/2007 |
| WO | 2008076839 A2 | 6/2008 |
| WO | 2008097599 A2 | 8/2008 |
| WO | 2013102021 A2 | 7/2013 |

OTHER PUBLICATIONS

Murray et al., "Microbial Inhibition on Hospital Garments Treated with Dow Corning 5700 Antimicrobial Agent," Journal of Clinical Microbiology, vol. 26, No. 9, Sep. 1988, pp. 1884-1886.
Rutala et al., "Guideline for Disinfection and Sterilization in Healthcare Facilities, 2008," Centers for Disease Control (CDC), Department of Health & Human Services, Feb. 15, 2017 (161 pages).
U.S. Food & Drug Administration (FDA), "Reprocessing Medical Devices in Health Care Settings: Validation Methods and Labeling Guidance for Industry and Food and Drug Administration Staff," Mar. 17, 2015 (44 pages).
European Commission, "Aerosol Dispensers Directive Evaluation—Background document", Sep. 23, 2016, Directorate-General for Internal Market, Industry, Entrepreneurship and SMEs, Belgium (1 page).
Monticello, Robert A., "The Use of Reactive Silane Chemistries to Provide Durable, Non-Leaching Antimicrobial Surfaces", AEGIS Environments, Midland, Michigan USA, Jan. 1, 2010 (77 pages).
AEGIS Environments, Material Safety Data Sheet AEGIS Microbe Shield(TM) Program—AEGIS(TM) Antimicrobial (Typical Application Strength), Midland, Michigan USA, May 12, 2004 (5 pages).

* cited by examiner

SPLINTING SYSTEM INCLUDING AN ANTIMICROBIAL COATING AND A METHOD OF MANUFACTURING THE SAME

BACKGROUND OF THE DISCLOSURE

A person can become injured in a manner that a health care professional would immobilize a body part of the person. A splint is a device that, when applied to the injured person, immobilizes the body part to which it is applied. For example, the person might injure his arm. The proper medical treatment might be to immobilize the arm about the elbow. The splint can then be applied from the wrist of the person, over the elbow, and toward the shoulder of the person. The splint helps prevent the arm from moving about the elbow. While fracture of a bone in the arm might lead to splinting, there could be other medical events that lead to splinting, such as burns, cuts, and other wounds.

Despite being used for health care purposes, splints are not sterilized. This is disadvantageous, because splints and the packaging for splints can harbor harmful microorganisms, such as bacteria and viruses. Those microorganisms might then be transferred to the injured person. This is especially problematic if the injured person has a cut or burn and the splint is applied over or near the cut or burn. Therefore, there is a need to prevent the splint and the packaging of the splint from being a source of bacteria and viruses that could enter into the wound and cause infection. In addition, because splints contact the skin of the person, the splint has a tendency to cause odor. Therefore, there is a further need to prevent the splint from causing odor.

BRIEF SUMMARY OF THE DISCLOSURE

According to a first aspect of the present disclosure, a splinting system comprises: a curable splint member including layers of fiberglass cloth coated with a water curable resin, and a pad at least partially enveloping the layers of fiberglass cloth, the pad having an exterior surface and an antimicrobial coating applied to the exterior surface; and a metal foil pouch containing the curable splint member, the metal foil pouch including an exterior surface; wherein, the antimicrobial coating includes a silane quaternary ammonium ion or salt thereof.

Embodiments of the first aspect of the disclosure can include any one or a combination of the following features:
the metal foil pouch further includes the antimicrobial coating applied to the exterior surface of the metal foil pouch;
the splinting system further comprises a clamp configured to selectively seal or unseal the metal foil pouch, the clamp including an exterior surface and the antimicrobial coating applied to the exterior surface of the clamp;
the pad comprises felted polypropylene fibers;
the water curable resin includes a polyurethane resin; and
the silane quaternary ammonium ion or salt thereof is one or more of:
3-(trimethoxysilyl)propyldimethyloctadecyl ammonium ion,
3-(trimethoxysilyl)propyldimethyloctadecyl ammonium chloride,
3-(trihydroxysilyl)propyldimethyloctadecyl ammonium ion, or
3-(trihydroxysilyl)propyldimethyloctadecyl ammonium chloride.

According to a second aspect of the present disclosure, a method of manufacturing a curable splint member having antimicrobial properties comprises: applying a solution, which includes a silane quaternary ammonium ion or salt thereof and a solvent, to an exterior surface of a pad; drying the pad; and at least partially enveloping layers of fiberglass cloth, which are coated with a water curable resin, within the pad.

Embodiments of the second aspect of the disclosure can include any one or a combination of the following features:
the solvent is isopropyl alcohol;
the isopropyl alcohol is between 30 percent to 90 percent by weight of the solution; and
the silane quaternary ammonium ion or salt thereof is one or more of:
3-(trimethoxysilyl)propyldimethyloctadecyl ammonium ion,
3-(trimethoxysilyl)propyldimethyloctadecyl ammonium chloride,
3-(trihydroxysilyl)propyldimethyloctadecyl ammonium ion, or
3-(trihydroxysilyl)propyldimethyloctadecyl ammonium chloride.

According to a third aspect of the present disclosure, a method of manufacturing a splinting system comprises: applying a solution, which includes a silane quaternary ammonium ion or salt thereof and a solvent, to an exterior surface of a pad; drying the pad; and enveloping layers of fiberglass cloth, which are coated with a water curable resin, with the pad to form a curable splint member; applying the solution to an exterior surface of a metal foil pouch; drying the metal foil pouch; placing the curable splint member in the metal foil pouch; and sealing the metal foil pouch; wherein, the silane quaternary ammonium ion or salt thereof is between 0.1 percent and 10 percent by weight of the solution.

Embodiments of the third aspect of the disclosure can include any one or a combination of the following features:
the solvent is isopropyl alcohol;
the isopropyl alcohol is between 30 percent to 90 percent by weight of the solution;
the silane quaternary ammonium ion or salt thereof is one or more of:
3-(trimethoxysilyl)propyldimethyloctadecyl ammonium ion,
3-(trimethoxysilyl)propyldimethyloctadecyl ammonium chloride,
3-(trihydroxysilyl)propyldimethyloctadecyl ammonium ion, or
3-(trihydroxysilyl)propyldimethyloctadecyl ammonium chloride;
the method further comprises applying the solution to an exterior surface of a clamp configured to selectively seal or unseal the metal foil pouch; and
the pad comprises felted polypropylene fibers.

These and other features, advantages, and objects of the present disclosure will be further understood and appreciated by those skilled in the art by reference to the following specification, claims, and appended drawings.

DETAILED DESCRIPTION

For purposes of description herein, it is to be understood that the specific devices and processes illustrated in the attached drawings, and described in the following specification are simply exemplary embodiments of the inventive concepts defined in the appended claims. Hence, physical characteristics relating to the embodiments disclosed herein are not to be considered as limiting, unless the claims expressly state otherwise.

Figure 1:
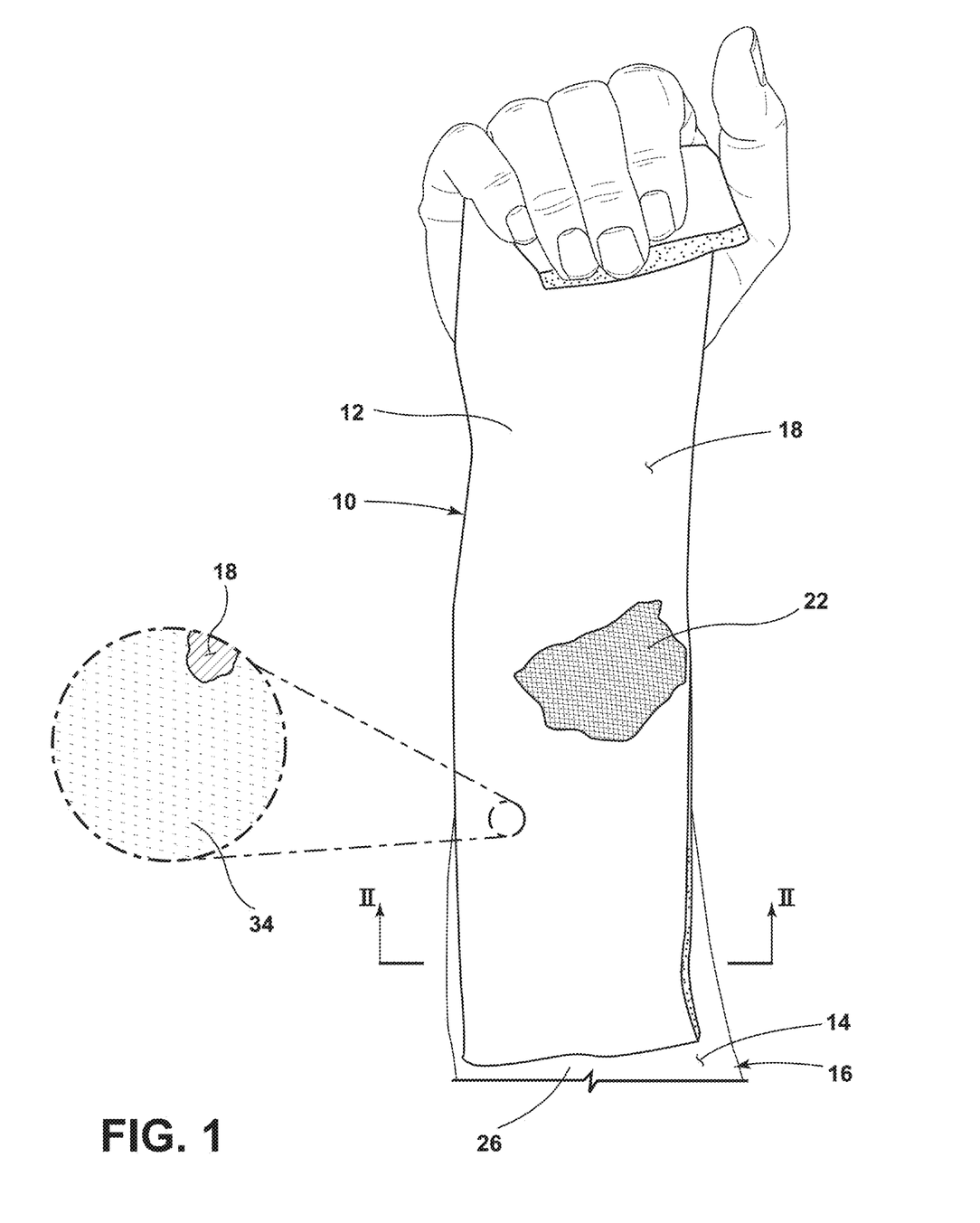
FIG. 1 is a front view of a curable splint member applied to an arm of a user, illustrating the curable splint member having a pad with an exterior surface, and an antimicrobial coating applied to the exterior surface.
Figure 2:
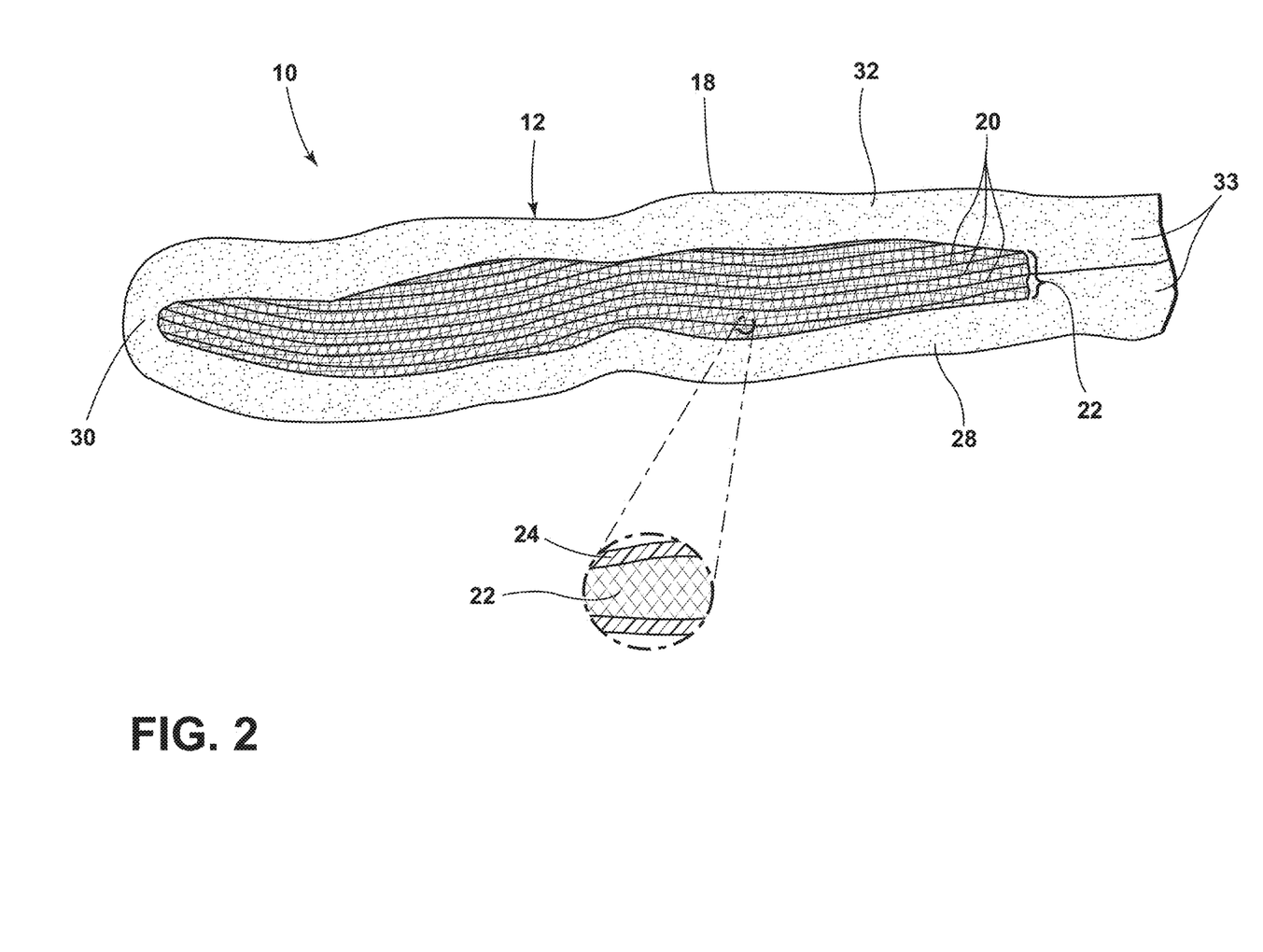
FIG. 2 is an elevational cross-sectional view of the curable splint member taken through line II-II of FIG. 1, illustrating the pad enveloping layers of fiberglass coated with a water activated resin.

Referring to FIGS. 1 and 2, a curable splint member 10 includes a pad 12. The pad 12 provides cushion and comfort when the curable splint member 10 is placed over skin 14 of a user 16. The pad 12 can be a felt, such as felted polypropylene fibers. However, the pad 12 can be any other moisture permeable material that would provide comfort to the user 16. The pad 12 has an exterior surface 18.

The curable splint member 10 further includes layers 20 of fiberglass cloth 22. A water curable resin 24 coats the layers 20 of fiberglass cloth 22. Upon application of water to the fiberglass cloth 22, such as by dipping the curable splint member 10 in water or spraying the curable splint member 10 with water, the water causes the water curable resin 24 to cure and become rigid. In some instances, moisture from surrounding air may provide the water to cure the resin 24. As an example, the water curable resin 24 can include be a polyurethane resin. While the resin 24 is curing, the curable splint member 10 can be molded to take the shape of the user 16 on which it is applied, such as an arm 26 of the user 16.

The pad 12 at least partially envelopes the layers 20 of fiberglass cloth 22. For example, the layers 20 of fiberglass cloth 22 can be placed upon a first portion 28 of the pad 12. The pad 12 can then be folded over at a fold 30, with a second portion 32 of the pad 12 placed over the layers 20 of fiberglass cloth 22. Side portions 33 can then be adhered (such as with tape) or stitched together. The pad 12 is porous to water, allowing water to reach the resin 24.

An antimicrobial coating 34 is applied to the exterior surface 18 of the pad 12. The antimicrobial coating 34 includes a silane quaternary ammonium ion or salt thereof. Preferred silane quaternary ammonium ions or salts thereof include 3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride. Applying the antimicrobial coating 34 to the exterior surface 18 of the pad 12 imparts antimicrobial properties on the exterior surface 18 and to the curable splint member 10 generally, which prevents or lessens the ability of the exterior surface 18 to harbor harmful microbes, viruses, bacteria, and the like and spread them to the user 16. Thus, applying the antimicrobial coating 34 acts as an illness prevention measure and also an odor prevention measure.

Figure 3:
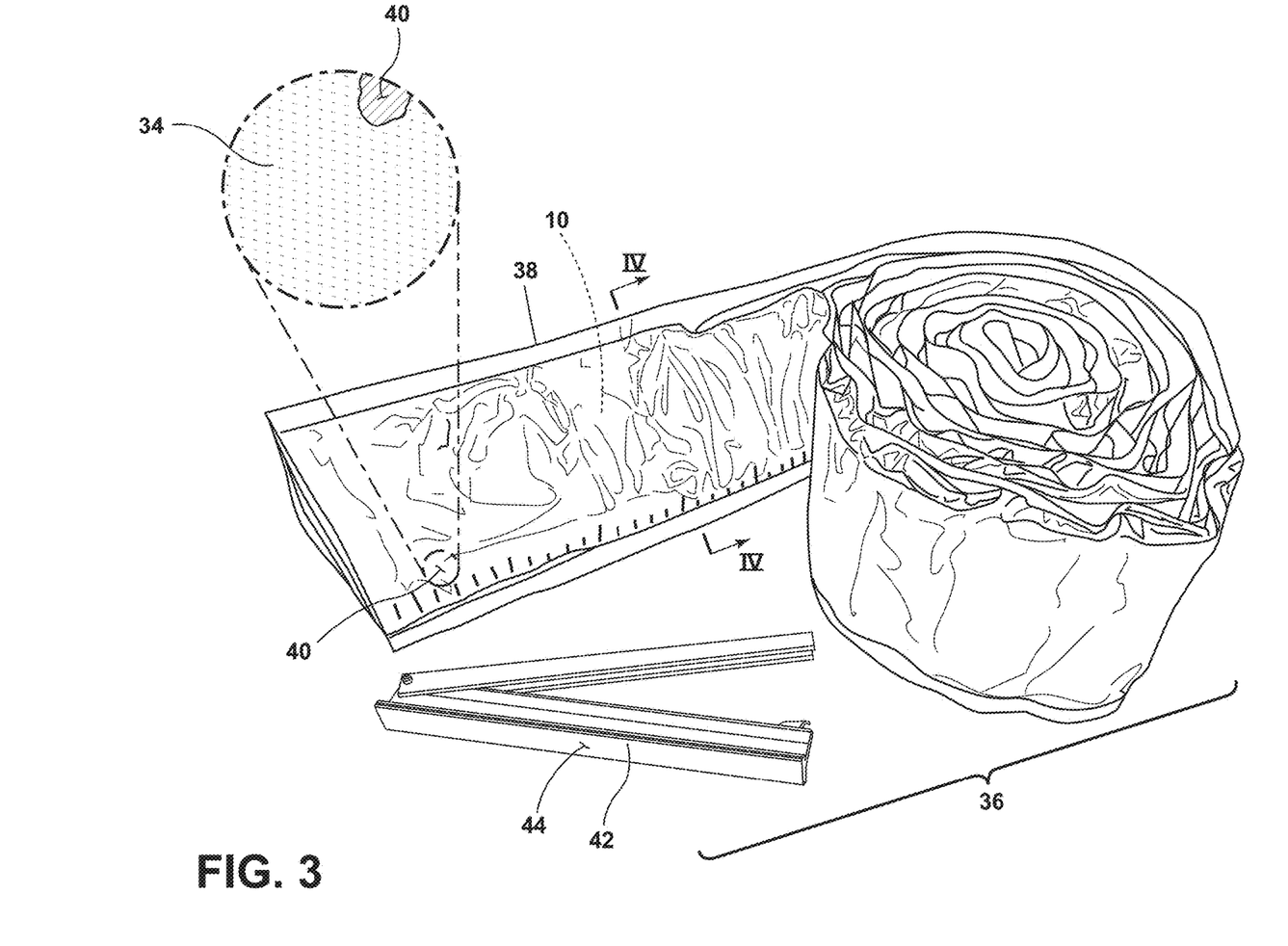
FIG. 3 is a perspective view of a splinting system that includes the curable splint member of FIG. 1, as well as a metal foil pouch that contains the curable splint member before application to the user, with the metal foil pouch having an exterior surface that is coated with the antimicrobial coating.
Figure 4:
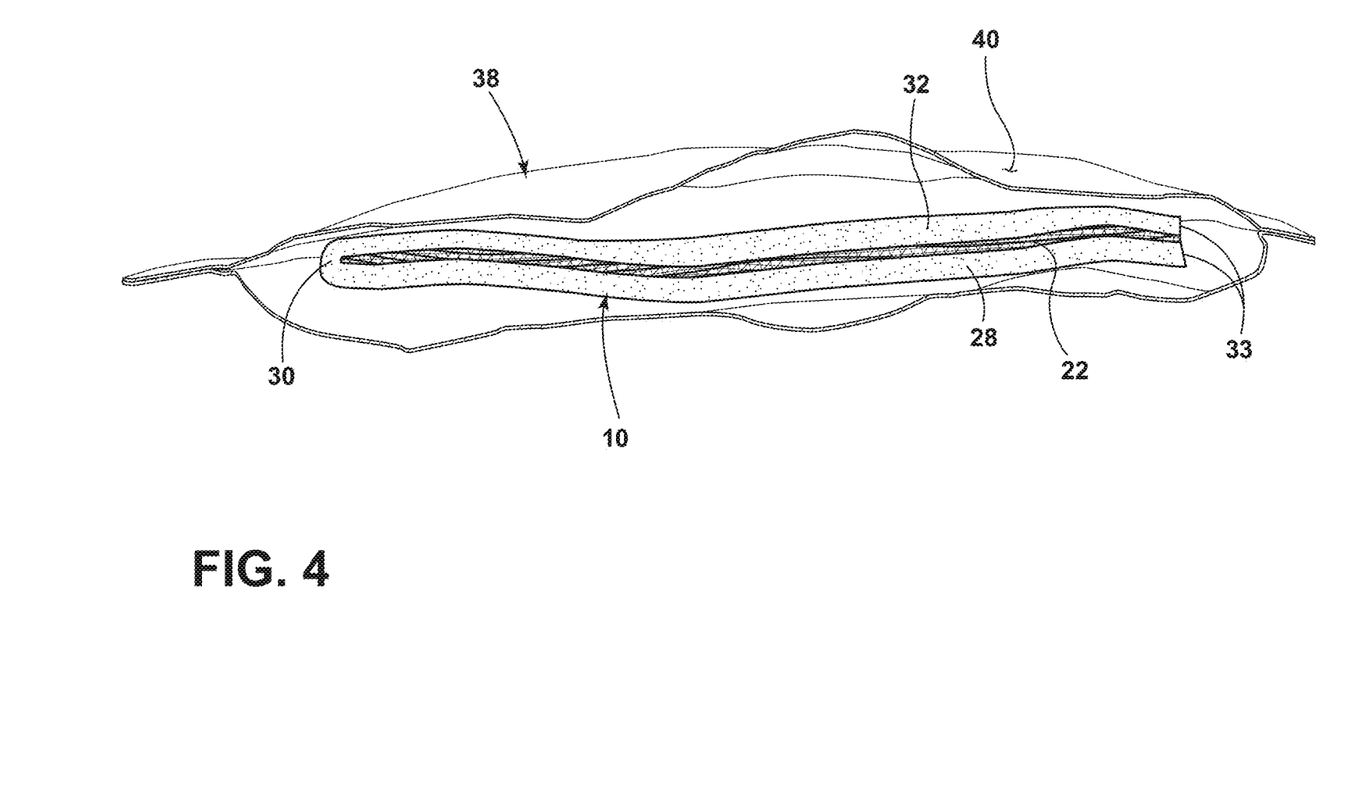
FIG. 4 is an elevational cross-sectional view of the metal foil pouch containing the curable splint member taken through line IV-IV of FIG. 3.
Figure 5:
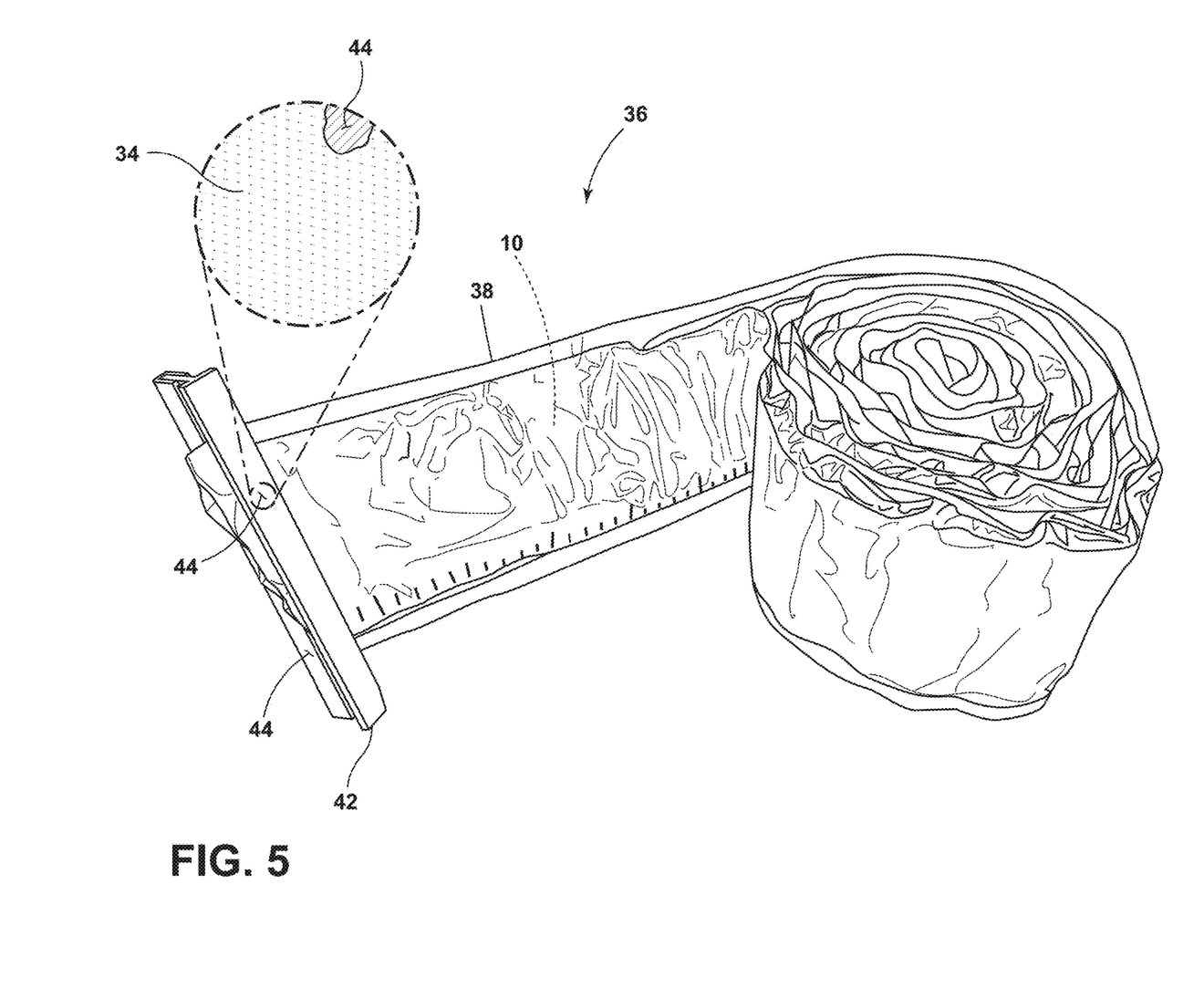
FIG. 5 is a perspective view of the splinting system of FIG. 3 further including a clamp to selectively close the metal foil pouch after the metal foil pouch has been open but an unused portion of the curable splint member still remains within the metal foil pouch, and the metal foil pouch having an exterior surface and the antimicrobial coating is applied to that exterior surface.

Referring now to FIGS. 3-5, the curable splint member 10 can be part of a splinting system 36. The splinting system 36 further includes a metal foil pouch 38. Before the curable splint member 10 is applied to the user 16, the metal foil pouch 38 contains the curable splint member 10. The metal foil pouch 38 reduces or eliminates moisture from the air from reaching the curable splint member 10, which would otherwise cause the curable splint member 10 to cure.

The metal foil pouch 38 includes an exterior surface 40. Like the exterior surface 18 of the pad 12, the antimicrobial coating 34 is applied to the exterior surface 40 of the metal foil pouch 38. The metal foil pouch 38 can be made from aluminum.

The splinting system 36 can further include a clamp 42. The clamp 42 can be applied to seal the metal foil pouch 38, such as when the metal foil pouch 38 is opened, a length of the curable splint member 10 is separated from a remainder, and the clamp 42 is applied to seal the metal foil pouch 38 with the remainder of the curable splint member 10 thus enclosed. The clamp 42 can be released to unseal the metal foil pouch 38. The clamp 42 has an exterior surface 44. The antimicrobial coating 34 is applied to the exterior surface 44 of the clamp 42.

The antimicrobial coating 34 on the metal foil pouch 38 and/or the clamp 42 reduces the likelihood of the splinting system 36 from spreading harmful microbes, viruses, bacteria, and the like to the user 16 or to others, such as when a health care provider opens the metal foil pouch 38 to apply the curable splint member 10 to the user 16, and uses the clamp 42 to seal the metal foil pouch 38.

Figure 6:
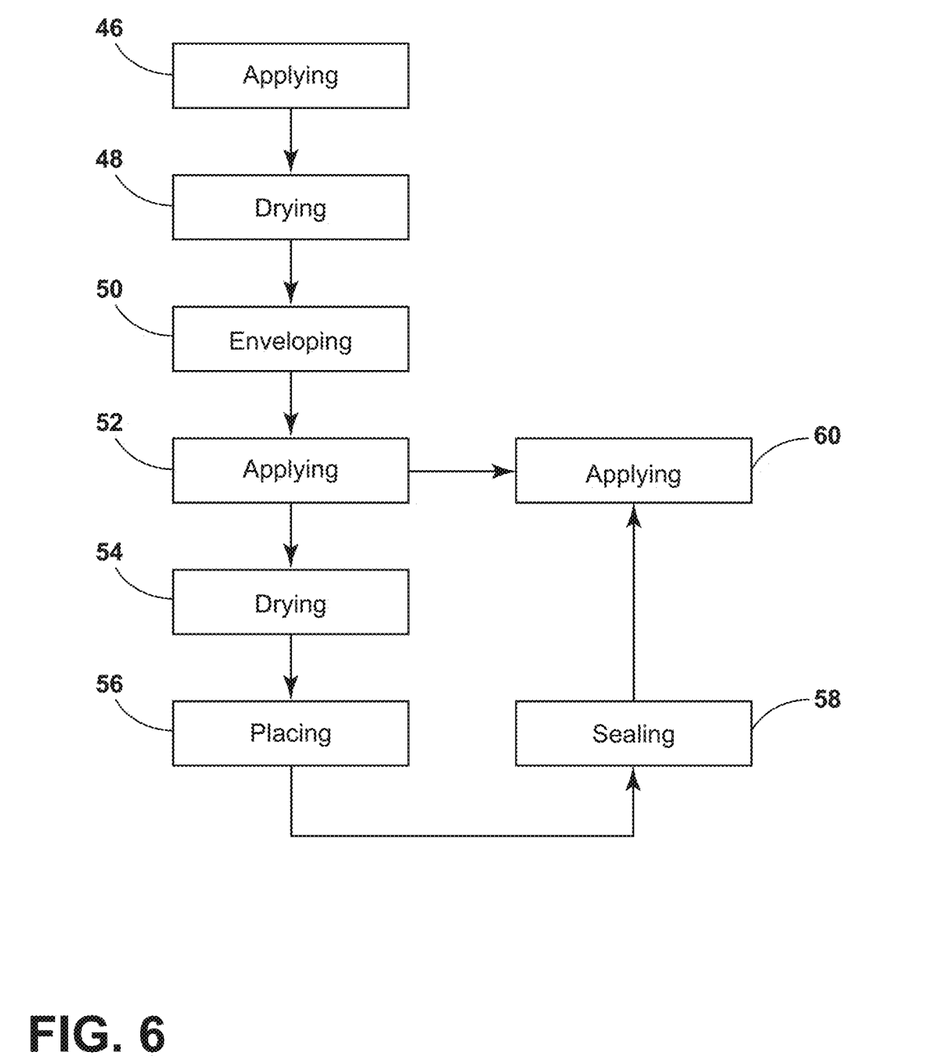
FIG. 6 is schematic flow diagram of a novel method of manufacturing the curable splint member of FIG. 1 and the splinting system of FIG. 3.

Referring now to FIG. 6, further described herein is a novel method of manufacturing the curable splint member 10 having antimicrobial properties. At step 46, the method includes applying a solution, which includes a silane quaternary ammonium ion or salt thereof and a solvent, to the exterior surface 18 of the pad 12. A preferred solvent is isopropyl alcohol. After application of the solution to the exterior surface 18, the solvent generally evaporates, which leaves the silane quaternary ammonium ion or salt thereof applied to the exterior surface 18. Again, preferred silane quaternary ammonium ions or salts thereof include 3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride. The solution can be applied to the exterior surface 18 via any application method, including electrostatic spraying, dipping, and coating.

The silane quaternary ammonium ion or salt thereof can comprise between 0.1 percent and 10 percent by weight of the solution. More preferably, the silane quaternary ammonium ion or salt thereof can comprise between 0.75 percent and 5 percent by weight of the solution. Even more preferably, the silane quaternary ammonium ion or salt thereof can comprise between 1.9 percent and 2.1 percent by weight of the solution.

As for the isopropyl alcohol, the isopropyl alcohol can comprise between 30 percent to 90 percent by weight of the solution. More preferably, the isopropyl alcohol can comprise between 55 percent and 65 percent by weight of the solution. An example preferable solution comprises (by weight) 60.0 percent isopropyl alcohol, 2.02 percent 3-(trimethoxysilyl)propyldimethyloctadecyl ammonium chloride, and 34.19 percent deionized water.

At step 48, the method further includes drying the pad 12. At step 50, the method further includes at least partially enveloping the layers 20 of fiberglass cloth 22 within the pad 12. This aspect is described above, with the layers 20 of fiberglass cloth 22 being laid upon the first portion 28 of the pad 12.

At an alternative step 52, the method further includes applying the solution to the exterior surface 40 of the metal foil pouch 38. Then, at step 54, the method further includes drying the metal foil pouch 38. So drying leaves the silane quaternary ammonium ion or salt thereof applied to the exterior surface 40. At step 56, the method further includes placing the curable splint member 10 in the metal foil pouch 38, and then at step 58, sealing the metal foil pouch 38. At another alternative step 60, the method further includes applying the solution to the exterior surface 44 of the clamp 42.

It is to be understood that variations and modifications can be made on the afore-mentioned structure without departing from the concepts of the present disclosure, and further it is to be understood that such concepts are intended to be covered by the following claims unless these claims by their language expressly state otherwise.

What is claimed is:

1. A method of manufacturing a splinting system comprising:
applying a solution, which comprises a silane quaternary ammonium ion or salt thereof and a solvent, to an exterior surface of a pad;
drying the pad;
enveloping layers of fiberglass cloth, which are coated with a water curable resin, with the pad to form a curable splint member;
applying the solution to an exterior surface of a metal foil pouch;
drying the metal foil pouch;
placing the curable splint member in the metal foil pouch; and
sealing the metal foil pouch;
wherein, the silane quaternary ammonium ion or salt thereof is between 0.1 percent and 10 percent by weight of the solution.

2. The method of claim 1,
wherein, the solvent is isopropyl alcohol.

3. The method of claim 2,
wherein, the isopropyl alcohol is between 30 percent to 90 percent by weight of the solution.

4. The method of claim 1,
wherein, the silane quaternary ammonium ion or salt thereof is one or more of: 3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride.

5. The method of claim 1 further comprising:
applying the solution to an exterior surface of a clamp configured to selectively seal or unseal the metal foil pouch.

6. The method of claim 1, wherein
the pad comprises felted polypropylene fibers.

* * * * *